US008303523B2

(12) United States Patent
Kudoh

(10) Patent No.: US 8,303,523 B2
(45) Date of Patent: Nov. 6, 2012

(54) WALKING ASSIST DEVICE

(75) Inventor: Hiroshi Kudoh, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 241 days.

(21) Appl. No.: 12/437,072

(22) Filed: May 7, 2009

(65) Prior Publication Data

US 2009/0281636 A1 Nov. 12, 2009

(30) Foreign Application Priority Data

May 8, 2008 (JP) ................................ 2008-122164

(51) Int. Cl.
*A61H 1/00* (2006.01)
*A61F 5/00* (2006.01)

(52) U.S. Cl. ................................ 601/5; 601/34; 602/16

(58) Field of Classification Search .................... 602/19, 602/16, 23, 26, 27; 601/5, 33, 34, 35, 23; 607/48, 49; 482/66, 128, 900–902; 702/127, 702/150; 434/247, 257
See application file for complete search history.

(56) References Cited

U.S. PATENT DOCUMENTS

| | | | | |
|---|---|---|---|---|
| 5,476,441 | A * | 12/1995 | Durfee et al. | 602/23 |
| 5,935,047 | A * | 8/1999 | Cawley | 482/79 |
| 6,699,209 | B2 * | 3/2004 | Turtzo | 602/27 |
| 6,935,991 | B1 * | 8/2005 | Mangino | 482/51 |
| 7,278,954 | B2 * | 10/2007 | Kawai et al. | 482/1 |
| 7,563,238 | B1 * | 7/2009 | Breashears | 602/27 |
| 7,578,799 | B2 * | 8/2009 | Thorsteinsson et al. | 602/5 |

FOREIGN PATENT DOCUMENTS

| | | |
|---|---|---|
| GB | 2278041 A * | 11/1994 |
| JP | 2007-020909 | 2/2007 |

* cited by examiner

*Primary Examiner* — Kevin C Sirmons
*Assistant Examiner* — Ophelia A Hawthorne
(74) *Attorney, Agent, or Firm* — Rankin, Hill & Clark LLP

(57) ABSTRACT

Provided is a walking assist device including a load transmit portion, a ground contacting portion capable of using a commercially available shoe, and a leg link disposed therebetween. The ground contacting portion is composed of a footboard for supporting the shoe thereon. The footboard is provided with a connection member connected to the leg link and a front holding member and a rear holding member for stably holding a front vamp portion and a rear vamp portion, respectively, of the shoe in an anteroposterior direction. When a pressure sensor for detecting a stepping force from a user is provided in the footboard, the front holding member is located ahead of the pressure sensor.

25 Claims, 3 Drawing Sheets

WALKING ASSIST DEVICE

PRIORITY CLAIM

The present application is based on and claims the priority benefit of Japanese Patent Application 2008-122164 filed on May 8, 2008, the contents of which are incorporated herein by reference in its entirety.

BACKGROUND OF THE INVENTION

1. Field of the Invention

The present invention relates to a walking assist device which assists a user in walking by alleviating a load acted on a leg thereof.

2. Description of the Related Art

Conventionally, there has been known a walking assist device having a load transmit portion, a ground contacting portion and a leg link disposed between the load transmit portion and the ground contacting portion, which assists a user in walking by alleviating a load acted on a leg thereof by means of supporting at least a part of the user's body weight by the leg link through the load transmit portion (for example, refer to Japanese Patent Laid-open No. 2007-20909).

In the conventional walking assist device, the ground contacting portion is composed of a special shoe provided with a connection member configured to connect with the leg link. Therefore, it is impossible to use a commercially available shoe in the conventional walking assist device, which makes it inconvenient in use since it is necessary to change to wear the special shoe every time when using the conventional walking assist device.

SUMMARY OF THE INVENTION

The present invention has been accomplished in view of the aforementioned problems, and it is therefore an object of the present invention to provide a walking assist device in which a commercially available shoe can be used.

To attain an object described above, the present invention provides a walking assist device having a load transmit portion, a ground contacting portion and a leg link disposed between the load transmit portion and the ground contacting portion, which at least a part of a user's body weight is supported by the leg link through the load transmit portion, wherein the ground contacting portion is composed of a footboard for supporting thereon a shoe; and the footboard is provided with a connection member for connecting with the leg link, a front holding member and a rear holding member for stably holding the shoe in an anteroposterior direction.

According to the present invention, the shoe is laid on the footboard and is held by the front holding member and the rear holding member in the anteroposterior direction to become integrated with the footboard. The shoe is subsequently connected with the leg link through the footboard and the connection member connected to the footboard. Therefore, the walking assist device can be used to assist walking by using a commercially available shoe without using a special shoe connected to the connection member, which makes it convenient in use.

The front holding member and the rear holding member may be designed to hold a protruded portion of a sole of the shoe in the anteroposterior direction, respectively. However, it is possible that a shoe may not have the protruded portions in the anteroposterior direction. Therefore, by configuring the front holding member to hold a front vamp portion of the shoe and the rear holding member to hold a rear vamp portion thereof, it is advantageous to use various kinds of shoes in the walking assist device.

Further, when a pressure sensor is disposed in the footboard to detect a stepping force by the user, it is desirable to locate at least a part of the front holding member which presses the shoe from the upper ahead of the pressure sensor. Thereby, a pressing force by the front holding member will not act on the pressure sensor, and consequently, the detection error on the stepping force by the pressure sensor becomes small, improving the detection accuracy of the stepping force.

DETAILED DESCRIPTION OF THE PREFERRED EMBODIMENTS

Figure 1:
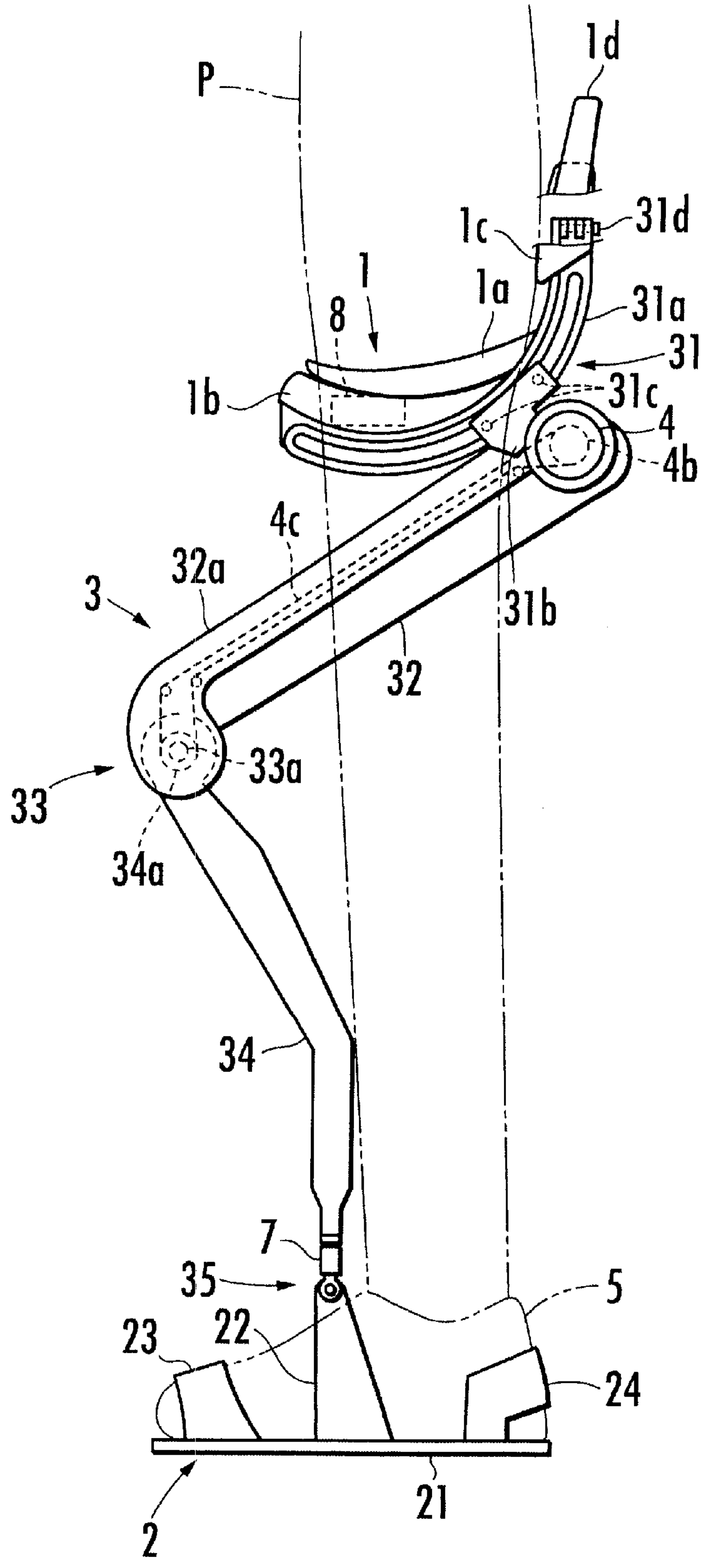
FIG. 1 is a side view of a walking assist device according to an embodiment of the present invention.
Figure 2:
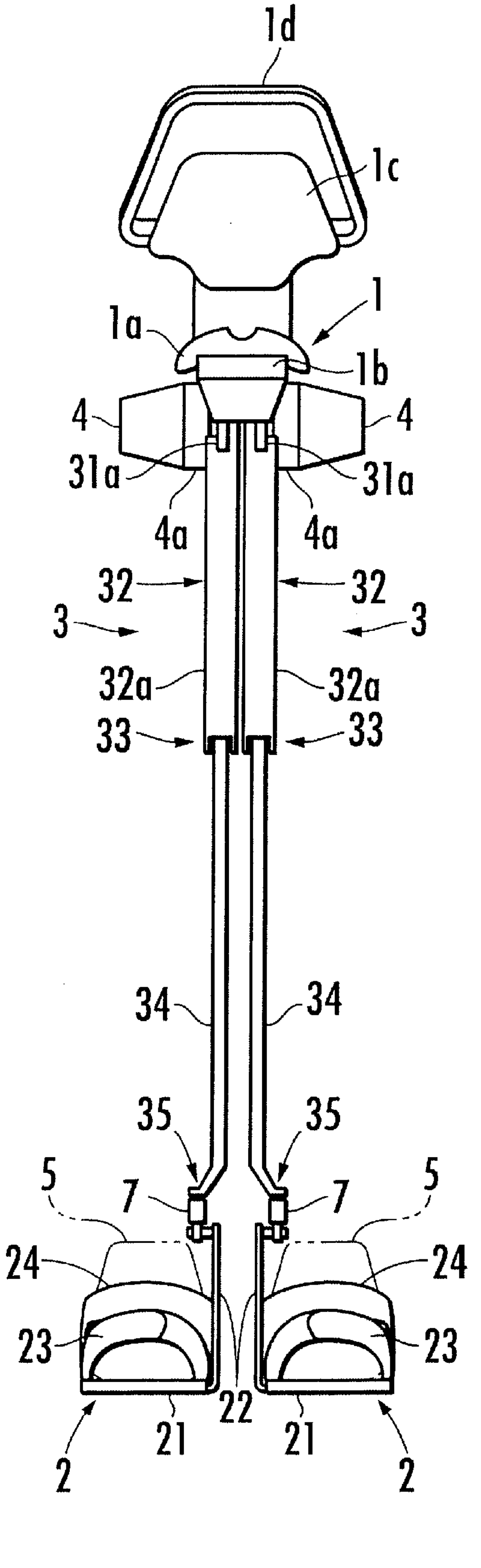
FIG. 2 is a front view of the walking assist device according to an embodiment of the present invention.

Hereinafter, a walking assist device according to an embodiment of the present invention will be described. As illustrated in FIG. 1 and FIG. 2, the walking assist device includes a seat member 1 on which a user P sits astride as a load transmit portion, a pair of left and right ground contacting portions 2 and 2, and a pair of left and right leg links 3 and 3 which are disposed between the seat member 1 and the two ground contacting portions 2 and 2, respectively.

Each leg link 3 can bend and stretch freely, composed of a first link member 32, and a second link member 34. The first link member 32 is connected to the seat member 1 through a first joint portion 31 at an upper end thereof, capable of swinging freely in the anteroposterior direction around the seat member 1. The second link member 34 is connected to a lower end of the first link member 32 through a rotary-typed second joint portion 33. A lower end of the second link member 34 is connected with a ground contacting portion 2 through a third joint portion 35 of a 3-axis structure.

The first link member 32 is provided with a driving source 4 for driving the second joint portion 33. Thereby, according to the rotation of the second joint portion 33 driven by the driving source 4, each leg link 3 is stretched to push the seat member 1 along a stretching direction upward so as to generate an assist force to support at least a part of a body weight of a user P (hereinafter, referred to as a body weight relieving assist force). The body weight relieving assist force generated in each leg link 3 is transmitted to the body trunk of the user P through the seat member 1 to relieve the load acted on a leg of the user P.

The driving source 4 is an electric motor provided with a reduction gear **4*a*, attached to a side surface of an upper end portion of the first link member 32. An output member of the reduction gear 4*a*, that is, a driving pulley 4*b* and a driven pulley 34*a* which is fixed concentrically with a joint axis 33*a* of the second joint portion 33 at the second link member 34 are connected through a wrapping transmission member 4*c*, such as a wire, a chain, a belt or the like. Thereby, a driving force output from the driving source 4 is transmitted to the second link member 34 through the wrapping transmission member 4***c* so that the second link member 34 swings around the joint axis 33*a* with respect to the first link member 32 to bend or stretch the leg link 3. Additionally, the first link member 32 is provided with a cover 32*a* configured to cover the wrapping transmission member 4*c*.

The seat member 1 is composed of a seat portion 1*a*, a support frame 1*b*, and a waist supporter 1*c*. The seat portion 1*a* is of a saddle shape to be seated by the user P. The support frame 1*b* is disposed below the seat portion 1*a* to support the seat portion 1*a*. The support frame 1*b* is configured to extend upward behind the seat portion 1*a* to form an uprising portion at a rear end thereof. The waist supporter 1*c* is disposed at the uprising portion. The waist supporter 1*c* is provided with a holding portion 1*d* of an arch shape to be held by the user P if necessary.

The first joint portion 31 at the upper end of each leg link 3 has a guide rail 31*a* of an arc shape disposed below the seat member 1. Then, each leg link 3 is movably engaged with the guide rail 31*a* via a plurality of rollers 31*c* pivotally attached to a slider 31*b* which is fixed to the upper end of the first link portion 32. In this way, each leg link 3 swings in the anteroposterior direction around the center of curvature of the guide rail 31*a* and the anteroposterior swing fulcrum of each leg link 3 functions as the center of curvature of the guide rail 31*a*.

Furthermore, the guide rail 31*a* is pivotally supported at the uprising portion formed at the rear end of the support frame 1*b* of the seat member 1 via a spindle 32*d* which is longitudinal in the anteroposterior direction. Therefore, the guide rail 31*a* is connected to the seat member 1, capable of swinging freely in the lateral direction. Accordingly, each leg link 3 is allowed to swing in the lateral direction, which enables the user P to abduct his/her legs. In addition, the center of curvature of the guide rail 31*a* and the axis line of the spindle 31*d* are both located above the seat portion 1*a*. Thereby, the seat member 1 can be prevented from inclining greatly in the vertical direction and in the lateral direction when the user P shifts his/her body weight.

Each ground contacting portion 2 is composed of a footboard 21 for supporting thereon a shoe 5 to be worn by each foot of the user P. The footboard 21 is provided with a connection member 22 connected to the lower end of the leg link 3 through the third joint portion 35. The footboard 21 is also provided with a front holding member 23 and a rear holding member 24 for stably holding the shoe 5 in the anteroposterior direction, that is, to prevent the shoe 5 from deviating in the anteroposterior direction.

Since the shoe 5 supported on the footboard 21 is held by the front holding member 23 and the rear holding member 24 in the anteroposterior direction, the footboard 21 is integral with the shoe 5. Consequently, the shoe 5 is essentially connected with the leg link 3, through the footboard 21 and the connected member 22 disposed at the footboard 21. Therefore, a commercially available shoe 5 can be used instead of a special shoe connected to the connection member. As a result thereof, it is convenient to use the walking assist device since it is not necessary to change to wear the special shoe every time when using the walking assist device.

Figure 3:
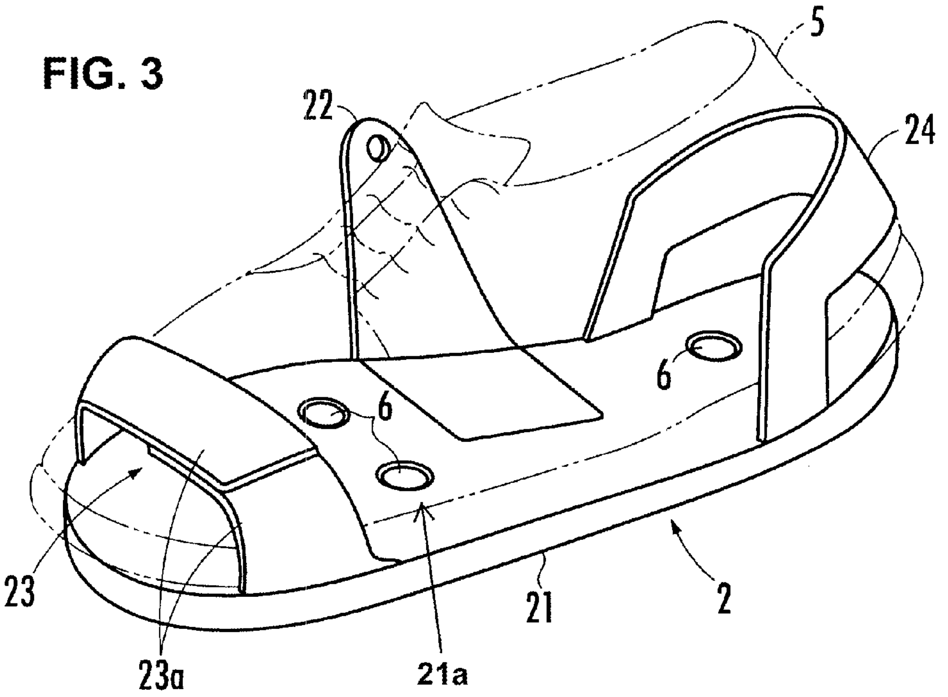
FIG. 3 is a perspective view of a ground contacting portion provided in the walking assist device according to an embodiment of the present invention.

Herein, it is possible to configure the front holding member 23 and the rear holding member 24 to hold a protruded portion from a sole of the shoe 5 in the anteroposterior direction, respectively. However, it is unable to cope with a shoe without such protruded portions in the anteroposterior direction in this configuration. Therefore, as illustrated in FIG. 3 of the present embodiment, by configuring the front holding member 23 to hold a front vamp portion of the shoe 5 and the rear holding member 24 to hold a rear vamp portion thereof, it is advantageous to use various kinds of shoes in the walking assist device.

The front holding member 23 is composed of a pair of laterally disposed bands 23*a* and 23*a*. Each band 23*a* is provided with a fastener. When the rear vamp portion of the shoe 5 is pushed to contact with the rear holding member 24, the pair of bands 23*a* and 23*a* of the front holding member 23 are tied up on the front vamp portion of the shoe 5 so as to hold the front vamp portion.

The rear holding member 24 is configured to have an inward inclination in the upward direction to have a surface contact with the rear vamp portion of the shoe 5. According thereto, the rear vamp portion of the shoe 5 can be certainly prevented from slipping out. Moreover, in case the rear holding member 24 is formed from a hard material, by attaching a friction material such as rubber or the like on the rear holding member 24 to be contacted by the rear vamp portion, the rear vamp portion of the shoe 5 can be further prevented from slipping out. It is possible to form the rear holding member 24 from a soft material such as rubber or the like to have the same shape as described in the present embodiment. It is also acceptable that the rear holding member 24 is composed of a pair of laterally disposed bands and each band is provided with a fastener so that the rear vamp portion of the shoe 5 is held by fastening the pair of bands.

In order to detect the stepping force from the user P, the footboard 21 is provided with three pressure sensors 6, in detail, two of them are located underneath the MP joints of the user's foot in the front (at an MP joint supporting portion 21*a* of the footboard 21), respectively, and one of them is located underneath the heel of the foot in the back. Moreover, a 2-axis force sensor 7 is built into the third joint portion 35. Detection signals from the pressure sensors 6 and the force sensor 7 are input to a controller 8 housed in the support frame 1*b* of the seat member 1. On the basis of the detection signals from the pressure sensors 6 and the force sensor 7, the controller 8 performs a walking assist control by controlling the driving source 4 to drive the second joint portion 33 of the leg link 3 to generate the body weight relieving assist force.

The body weight relieving assist force is acted on a connection line (hereinafter, referred to as a reference line) joining a swing fulcrum of the leg link 3 with respect to the first joint portion 31 in the anteroposterior direction and a swing fulcrum of the leg link 3 with respect to the third joint portion 35 in the anteroposterior direction. In the walking assist control, the actual body weight assist force acted on the reference line (accurately, a resultant force between the body weight relieving assist force and a force generated by the weights of the seat member 1 and each leg link 3) is calculated based on detection values of forces in the two-axis direction detected by the force sensor 7. Thereafter, on the basis of the stepping force detected by the pressure sensors 6 in each ground contacting portion 2, a ratio of the stepping force of each leg with respect to the resultant force from both legs of the user P is calculated. Then, a desired control value of the body weight relieving assist force which should be generated for each leg link 3 is calculated by multiplying a predefined value of the body weight relieving assist force by the calculated ratio of the stepping force of each leg. Subsequently, the driving source 4 is controlled so as to make the actual body weight relieving assist force calculated on the basis of the detection values by the force sensor 7 approximate to the desired control value.

Figure 4:
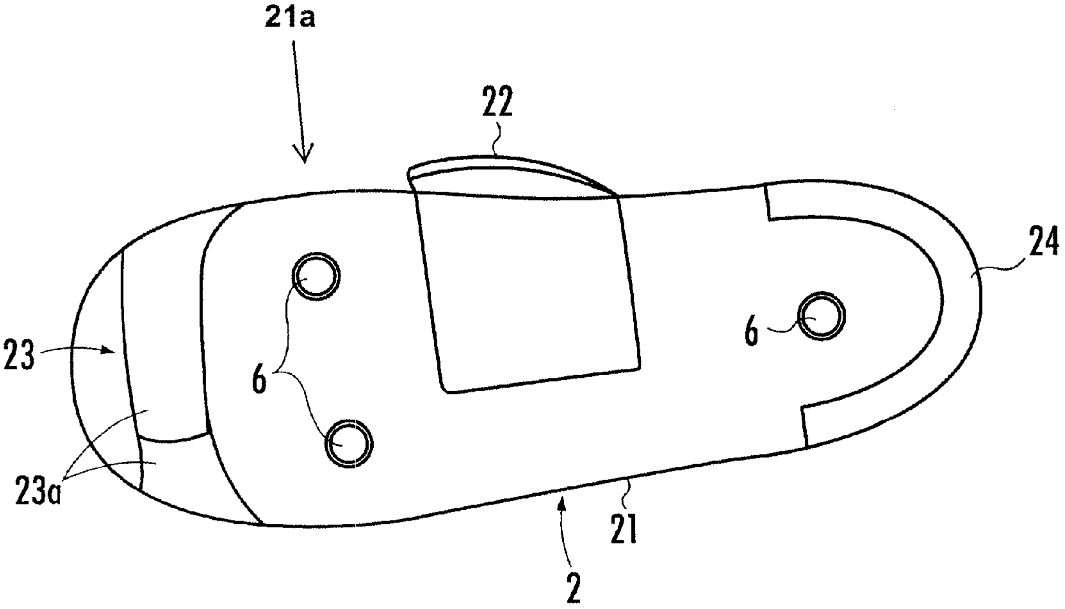
FIG. 4 is plan view of the ground contacting portion provided in the walking assist device according to an embodiment of the present invention.

Herein, if a pressing force generated by the front holding member 23 is acted on the pressure sensors 6, the detection accuracy of the stepping force will be deteriorated. Therefore, as illustrated in FIG. 4, the front holding member 23 is located ahead of the pressure sensors 6 in the front in the present embodiment. According thereto, the pressing force by the front holding member 23 is not acted on the pressure sensors 6, the detection error becomes small, and consequently, the detection accuracy of the stepping force is improved. Note that as long as a part of the front holding member 23 which holds the shoe 5 from the upper is located ahead of the pressure sensors 6, it is acceptable that a basal connection portion of the front holding member 23, through which the front holding member 23 is jointed to the ground contacting portion 2, is located behind the pressure sensors 6. In other words, even though the basal connection portion of the front holding member 23 is located behind the pressure sensors 6, the pressing force will not be acted on the pressure sensors 6 from above, therefore, the detection accuracy of the stepping force will not be affected. Herein, the part of the front holding member 23 which holds the shoe 5 from the upper is referred to as the part which has contact to the shoe 5 and applies a downward force to the shoe 5.

Although the embodiment of the present invention has been described hereinabove with reference to the drawings, the present invention is not limited thereto. For example, in the above-mentioned embodiment, the leg link 3 is configured as a telescopic link with a rotary second joint portion 33 disposed therein; it is acceptable that the leg link is configured as a telescopic link having a linear second joint portion. In addition, it is possible to adopt a harness mounted around the waist of the user as the load transmit portion. Moreover, in order to assist the walking of a handicapped user whose one leg is crippled due to bone fracture or the like, it is possible to leave only one leg link of the left and right leg links 3 and 3 in the above-mentioned embodiment corresponding to the crippled leg of the user by removing the other.

What is claimed is:

1. A walking assist device having a load transmit portion, a ground contacting portion and a leg link disposed between the load transmit portion and the ground contacting portion, the walking assist device configured such that at least a part of a user's body weight is supported by the leg link through the load transmit portion, wherein the ground contacting portion is composed of a footboard adapted to support a shoe thereon, said footboard having an MP joint supporting portion configured to be disposed directly below a user's MP joint when the shoe is supported on the footboard, said MP joint supporting portion being only that portion of the footboard disposed directly below the user's MP joint when the shoe is supported on the footboard; and the footboard is provided with a connection member for connecting with the leg link, and front and rear holding members configured to stably hold the shoe in an anteroposterior direction on the footboard, said front holding member composed of a pair of laterally-disposed bands and disposed in a forward direction relative to the MP joint supporting portion of the footboard so as to be disposed between the MP joint supporting portion and a front end of the footboard in an anteroposterior direction, the pair of laterally-disposed bands of the front holding member configured to be tiled on a front vamp portion of the shoe to hold the front vamp portion of the shoe.

2. The walking assist device according to claim 1, wherein the leg link further comprises:

a first link member;

a first joint portion connecting a first end of the first link member to the load transmit portion;

a second link member;

a second joint portion connecting a first end of the second link member to a second end of the first link member; and a third joint portion connecting a second end of the second link member to the ground contacting portion.

3. The walking assist device according to claim 2, wherein the first joint portion is configured to allow the first link member to swing in an anteroposterior direction around the load transmit portion, the second joint portion is a rotary-typed joint portion, and the third joint portion has a three-axis structure.

4. The walking assist device according to claim 2, wherein the load transmit portion comprises a seat member having a saddle shape.

5. The walking assist device according to claim 1, wherein the rear holding member is configured to hold a rear vamp portion of the shoe and comprises a heel abutting portion having a surface adapted to directly abut a rear end of the shoe when the shoe is supported on the footboard and held by the front and rear holding members, said surface of the heel abutting portion being inclined in the forward direction toward the front holding member so as to define an acute angle with a surface of a rear portion of the footboard which is adapted to have a heel of the shoe rest thereon when the shoe is supported on the footboard and held by the front and rear holding members.

6. The walking assist device according to claim 5, wherein the heel abutting portion includes a friction material positioned to contact the rear end of the shoe when the shoe is supported on the footboard and held by the front and rear holding members.

7. The walking assist device according to claim 1, wherein the load transmit portion is configured to engage a torso of the user.

8. The walking assist device according to claim 7, wherein the load transmit portion comprises a seat member having a saddle shape.

9. The walking assist device according to claim 1, wherein the footboard is provided with a pressure sensor for detecting a stepping force by the user, said pressure sensor disposed in the MP joint supporting portion of the footboard such that the pressure sensor is configured to sense a pressure applied to the footboard from the user's MP joint, the pressure sensor disposed in a rearward position on the footboard relative to the front holding member so as to be disposed between the front holding member and a rear end of the footboard, which is opposite to the front end of the footboard in the anteroposterior direction, the pair of laterally-disposed bands of the front holding member configured to press the shoe from the upper toward the footboard when the shoe is supported on the footboard and held by the pair of laterally-disposed bands of the front holding member, and the pressure from the user's MP joint is applied to the footboard at the rearward position on the footboard relative to the front holding member when the shoe is supported on the footboard and held by the front and rear holding members.

10. The walking assist device according to claim 1, further comprising an MP joint pressure sensor disposed in the MP joint supporting portion of the footboard, wherein the front holding member is entirely disposed in the forward direction relative to the MP joint pressure sensor on the footboard, the MP joint pressure sensor is disposed in the forward direction relative to the connection member on the footboard such that the connection member is disposed between the MP joint pressure sensor and a rear end of the footboard, which is opposite to the front end of the footboard in the anteroposterior direction, and the rear holding member is disposed in a rearward direction relative to the connection member on the footboard.

11. The walking assist device according to claim 1, wherein the footboard is provided with a plurality of pressure sensors for detecting a stepping force by the user, said plurality of pressure sensors including a forward-most pressure sensor disposed nearest the front end of the footboard and in the MP joint supporting portion of the footboard such that the front holding member, which is configured to press the shoe from the upper toward the footboard when the shoe is supported on the footboard and held by the front holding member, is entirely disposed in the forward direction on the footboard relative to the forward-most pressure sensor.

12. The walking assist device according to claim 1, wherein the leg link includes right and left leg links, each of which is formed of a first link member swingably connected to the load transmit portion via a first joint portion so as to be swingable in a front-back direction, and a second link member connected to a lower end of the first link member via a rotary second joint portion, and wherein the front holding member is disposed directly below the rotary second joint portion in the anteroposterior direction when viewed from a side while the walking assist device is worn by the user and the user is in a standing state.

13. The walking assist device according to claim 1, wherein an entirety of the front holding member is disposed in the forward direction on the footboard relative to the MP joint supporting portion of the footboard.

14. The walking assist device according to claim 1, wherein the footboard extends in the anteroposterior direction from the front end of the footboard to a rear end of the footboard.

15. A ground contacting member of a walking assist device, wherein the ground contacting member comprises:

a footboard adapted to support a shoe thereon, said footboard having an MP joint supporting portion configured to be disposed directly below a user's MP joint when the shoe is supported on the footboard, said MP joint supporting portion being only that portion of the footboard disposed directly below the user's MP joint when the shoe is supported on the footboard;

a connection member connecting the footboard to the walking assist device; and a holding member adapted to secure the footboard to the shoe of a user, said holding member including front and rear holding members configured to stably hold the shoe in an anteroposterior direction on the footboard, said front holding member being disposed in a forward direction relative to the MP joint supporting portion of the footboard so as to be disposed between the MP joint supporting portion and a front end of the footboard in an anteroposterior direction, the front holding member configured to hold a front vamp portion of the shoe, and said rear holding member configured to hold a rear vamp portion of the shoe.

16. The ground contacting member according to claim 15, wherein the rear holding member includes a heel abutting portion having a surface adapted to directly abut a rear end of the shoe when the shoe is supported on the footboard and held by the front and rear holding members, said surface of the heel abutting portion being inclined in the forward direction toward the front holding member so as to define an acute angle with a surface of a rear portion of the footboard which is adapted to have a heel of the shoe rest thereon when the shoe is supported on the footboard and held by the front and rear holding members.

17. The ground contacting member according to claim 16, wherein the rear holding member is adapted to wrap around the rear vamp portion of the shoe when the shoe is supported on the footboard and held by the front and rear holding members.

18. The ground contacting member according to claim 16, wherein the heel abutting portion includes a friction material positioned to contact the rear end of the shoe when the shoe is supported on the footboard and held by the front and rear holding members.

19. The ground contacting member according to claim 15, wherein the front holding member further comprises:

a first band attached to a first side portion of the footboard at a position disposed in the forward direction relative to the MP joint supporting portion of the footboard;

a second band attached to a second side portion of the footboard at a position disposed in the forward direction relative to the MP joint supporting portion of the footboard; and a fastener provided on at least one of the first band and the second band, wherein the fastener is adapted to fasten the first band to the second band so as to allow the front holding member to vary in length.

20. The ground contacting member according to claim 19, wherein the rear holding member is adapted to wrap around the rear vamp portion of the shoe when the shoe is supported on the footboard and held by the front and rear holding members.

21. The ground contacting member according to claim 15, wherein the footboard is provided with a pressure sensor for detecting a stepping force by the user, said pressure sensor disposed in the MP joint supporting portion of the footboard such that the pressure sensor is configured to sense a pressure applied to the footboard from the user's MP joint, the pressure sensor disposed in a rearward direction relative to the front holding member so as to be disposed between the front holding member and a rear end of the footboard, which is opposite to the front end of the footboard in the anteroposterior direction; and the front holding member is configured to press an upper portion of the shoe toward the footboard at a position on the footboard disposed in the forward direction relative to a position at which the user's MP joint applies pressure to the footboard when the shoe is supported on the footboard and the held by the front holding member.

22. The ground contacting member according to claim 15, further comprising an MP joint pressure sensor disposed in the MP joint supporting portion of the footboard, wherein the front holding member is entirely disposed in the forward direction relative to the MP joint pressure sensor on the footboard, the MP joint pressure sensor is disposed in the forward direction relative to the connection member on the footboard such that the connection member is disposed between the MP joint pressure sensor and a rear end of the footboard, which is opposite to the front end of the footboard in the anteroposterior direction, and the rear holding member is disposed in a rearward direction relative to the connection member.

23. The ground contacting member according to claim 15, wherein the footboard is provided with a plurality of pressure sensors for detecting a stepping force by the user, said plurality of pressure sensors including a forward-most pressure sensor disposed nearest a the front-end of the footboard and in the MP joint supporting portion of the footboard such that the front holding member, which is configured to press the shoe from the upper toward the footboard when the shoe is supported on the footboard and held by the front holding member, is entirely disposed in the forward direction relative to the forward-most pressure sensor.

24. The ground contacting member according to claim 15, wherein an entirety of the front holding member is disposed in the forward direction on the footboard relative to the MP joint supporting portion of the footboard.

25. The ground contacting member according to claim 15, wherein the footboard extends in the anteroposterior direction from the front end of the footboard to a rear end of the footboard.

* * * * *